United States Patent
Wu

(10) Patent No.: US 9,475,387 B2
(45) Date of Patent: Oct. 25, 2016

(54) DRUNK DRIVING PREVENTION SYSTEM AND METHOD WITH EYE SYMPTOM DETECTOR

(71) Applicant: Roger Li-Chung Wu, West Covina, CA (US)

(72) Inventor: Roger Li-Chung Wu, West Covina, CA (US)

(*) Notice: Subject to any disclaimer, the term of this patent is extended or adjusted under 35 U.S.C. 154(b) by 95 days.

(21) Appl. No.: 14/215,036

(22) Filed: Mar. 16, 2014

(65) Prior Publication Data

US 2015/0258892 A1    Sep. 17, 2015

(51) Int. Cl.
| | |
|---|---|
| *G08B 21/00* | (2006.01) |
| *B60K 28/06* | (2006.01) |
| *A61B 5/18* | (2006.01) |
| *A61B 5/00* | (2006.01) |
| *A61B 3/113* | (2006.01) |
| *A61B 5/107* | (2006.01) |

(52) U.S. Cl.
CPC .............. *B60K 28/06* (2013.01); *A61B 3/113* (2013.01); *A61B 5/1075* (2013.01); *A61B 5/18* (2013.01); *A61B 5/489* (2013.01); *A61B 5/746* (2013.01)

(58) Field of Classification Search
CPC .. B60K 28/063; B60K 28/06; B60K 28/066; B60K 28/00; B60W 2540/24; G08B 21/06; G08B 21/02
USPC .......................................................... 340/576
See application file for complete search history.

(56) References Cited

U.S. PATENT DOCUMENTS

| | | | | |
|---|---|---|---|---|
| 4,005,398 | A * | 1/1977 | Inoue .................... | B60K 28/06 180/272 |
| 7,027,621 | B1 * | 4/2006 | Prokoski ............ | G06K 9/00255 180/272 |
| 2008/0243558 | A1 * | 10/2008 | Gupte .................... | G06Q 40/08 705/4 |
| 2010/0028210 | A1 * | 2/2010 | Ozaki .................. | B60K 28/063 422/84 |
| 2010/0090839 | A1 * | 4/2010 | Omi ...................... | B60K 28/04 340/575 |
| 2013/0069773 | A1 * | 3/2013 | Li .......................... | B60K 28/02 340/426.1 |
| 2013/0135109 | A1 * | 5/2013 | Sharon .................. | G08B 21/02 340/576 |

* cited by examiner

*Primary Examiner* — Mark Rushing
(74) *Attorney, Agent, or Firm* — Raymond Y. Chan; David and Raymond Patent Firm

(57) ABSTRACT

A drunk driving prevention system for a vehicle includes an eye symptom detector adapted for supporting in the vehicle at a position to detect eye symptoms of a driver, a control module operatively linked to the eye symptom detector for determining and analyzing whether the eye symptoms of the driver match with alcohol influenced eye symptoms, and a signal module operatively linked control module for generating a drunk driving signal in response to the alcohol influenced eye symptoms that suspect an alcohol concentration of the driver is above a predetermined threshold.

27 Claims, 4 Drawing Sheets

DRUNK DRIVING PREVENTION SYSTEM AND METHOD WITH EYE SYMPTOM DETECTOR

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

The present invention relates to a safety device for vehicle, and more particular to a drunk driving prevention system and method, which detects the eye activity of the driver in the sense of determining the presence of alcohol for indicating whether the driver is capable of driving the vehicle safely.

2. Description of Related Arts

Driving under the influence (DUI), commonly called "drunk driving" refers to operating a vehicle while one's blood alcohol content is above the legal limit set by state. Every year, ten thousands of people were killed and more than hundred thousands of people were injured due to drunk driving. Every single injury and death caused by drunk driving is totally preventable. Recently, anti-drunk driving apparatuses to eliminate drunk driving are provided.

For example, an alcohol sensor is considered as one of the popular anti-drunk driving apparatuses to be installed into the vehicle, wherein when the driver is guided to blow a breath to the alcohol sensor, the alcohol sensor will measure the alcohol concentration. If the alcohol concentration measured by the alcohol sensor is higher than a predetermined threshold, an ignition interlock is activated to stop the ignition of the vehicle. In other words, the alcohol sensor can be deactivated only when the alcohol concentration measured is below the predetermined threshold to start the vehicle. However, such alcohol sensor has a drawback that even though the driver under the influence can start and drive the vehicle by having other person to blow a breath to the alcohol sensor instead of the driver in order to deactivate the alcohol sensor.

The alcohol sensor is not accurate and will falsely determine the alcohol concentration of the driver by blown breath. For example, after the driver rinses his or her mouth in the morning by a mouth rinse which contains alcohol as one of the ingredients, the alcohol concentration measured by the alcohol sensor will be higher than the predetermined threshold.

Furthermore, the drunk driver can cheat the alcohol sensor by any filter at the mouthpiece of the alcohol sensor when blowing the breath thereto. Therefore, the measured alcohol concentration by the alcohol sensor is lower than the actuate alcohol concentration of the driver because of the filter.

The alcohol sensor can only stop the ignition of the vehicle. Once the vehicle is start, the drunk driver is able to drive the vehicle. In other words, there is no prevention to stop the drunk driver while driving.

SUMMARY OF THE PRESENT INVENTION

The invention is advantageous in that it provides a drunk driving prevention system and method, which detects the eye activity of the driver in the sense of determining the presence of alcohol for indicating whether the driver is capable of driving the vehicle safely.

Another advantage of the invention is to a drunk driving prevention system and method, wherein the eye activity of the driver can be the eye movements of the driver to be detector in order to determine and analyze whether the eye movements of the driver are involuntary eye movements that suspects an alcohol concentration of said driver is above a predetermined threshold.

Another advantage of the invention is to a drunk driving prevention system and method, wherein eyeball movements, sizes of pupils, ocular conjunctival blood vessel of the driver are also be detected as parts of the eye symptoms to accurately determine whether the eye symptoms of the driver are alcohol influenced eye symptoms.

Another advantage of the invention is to a drunk driving prevention system and method, wherein the eye symptom detector is remained activated before the vehicle is start until the vehicle is turned off, so as to extend the detection period for the driver.

Another advantage of the invention is to a drunk driving prevention system and method, wherein a sobriety test is executed to guide the driver to perform in order to detect the eye movements of the driver.

Another advantage of the invention is to a drunk driving prevention system and method, wherein when the alcohol influenced eye symptoms are determined, the igniter or starter of the vehicle will be automatically deactivated for preventing an ignition of the vehicle.

Another advantage of the invention is to a drunk driving prevention system and method, wherein an image of the driver's face will be captured when the eye symptom detector detects the eye symptoms of the driver in order to identify the driver of the vehicle.

Another advantage of the invention is to a drunk driving prevention system and method, wherein a suspected drunk driving signal will be automatically sent to a police or a drunk driving control organization when the alcohol influenced eye symptoms are kept detecting for a predetermined control time period.

Another advantage of the invention is to a drunk driving prevention system and method, which does not require to alter the original structural design of the vehicle, so as to minimize the manufacturing cost of the drunk driving prevention system incorporating with the vehicle. In other words, the drunk driving prevention system of the present invention can be an add-on system to install into any existing vehicle or can be a built-in system pre-installed into any new vehicle.

Another advantage of the invention is to a drunk driving prevention system and method, wherein no expensive or complicated structure is required to employ in the present invention in order to achieve the above mentioned objects. Therefore, the present invention successfully provides an economic and efficient solution for preventing any drunk driver to drive the vehicle.

Additional advantages and features of the invention will become apparent from the description which follows, and may be realized by means of the instrumentalities and combinations particular point out in the appended claims.

According to the present invention, the foregoing and other objects and advantages are attained by a drunk driving prevention system for a vehicle, comprising:

an eye symptom detector adapted for supporting in the vehicle at a position to detect eye symptoms of a driver;

a control module operatively linked to the eye symptom detector for determining and analyzing whether the eye symptoms of the driver are alcohol influenced eye symptoms; and a signal module operatively linked control module for generating a drunk driving signal in response to the alcohol influenced eye symptoms of the driver that suspects an alcohol concentration of the driver is above a predetermined threshold.

In accordance with another aspect of the invention, the present invention comprises a drunk driving prevention method for preventing drunk driving a vehicle, comprising the following steps.

(1) Detect eye symptoms of a driver by an eye symptom detector.

(2) Analyze whether the eye symptoms of the driver are alcohol influenced eye symptoms by a control module.

(3) If the eye symptoms of the driver detected are considered as normal eye symptoms, the driver is able to drive the vehicle.

(4) Generate a drunk driving signal by a signal generator if the eye movements of the driver detected as alcohol influenced eye symptoms that suspects an alcohol concentration of the driver is above a predetermined threshold.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
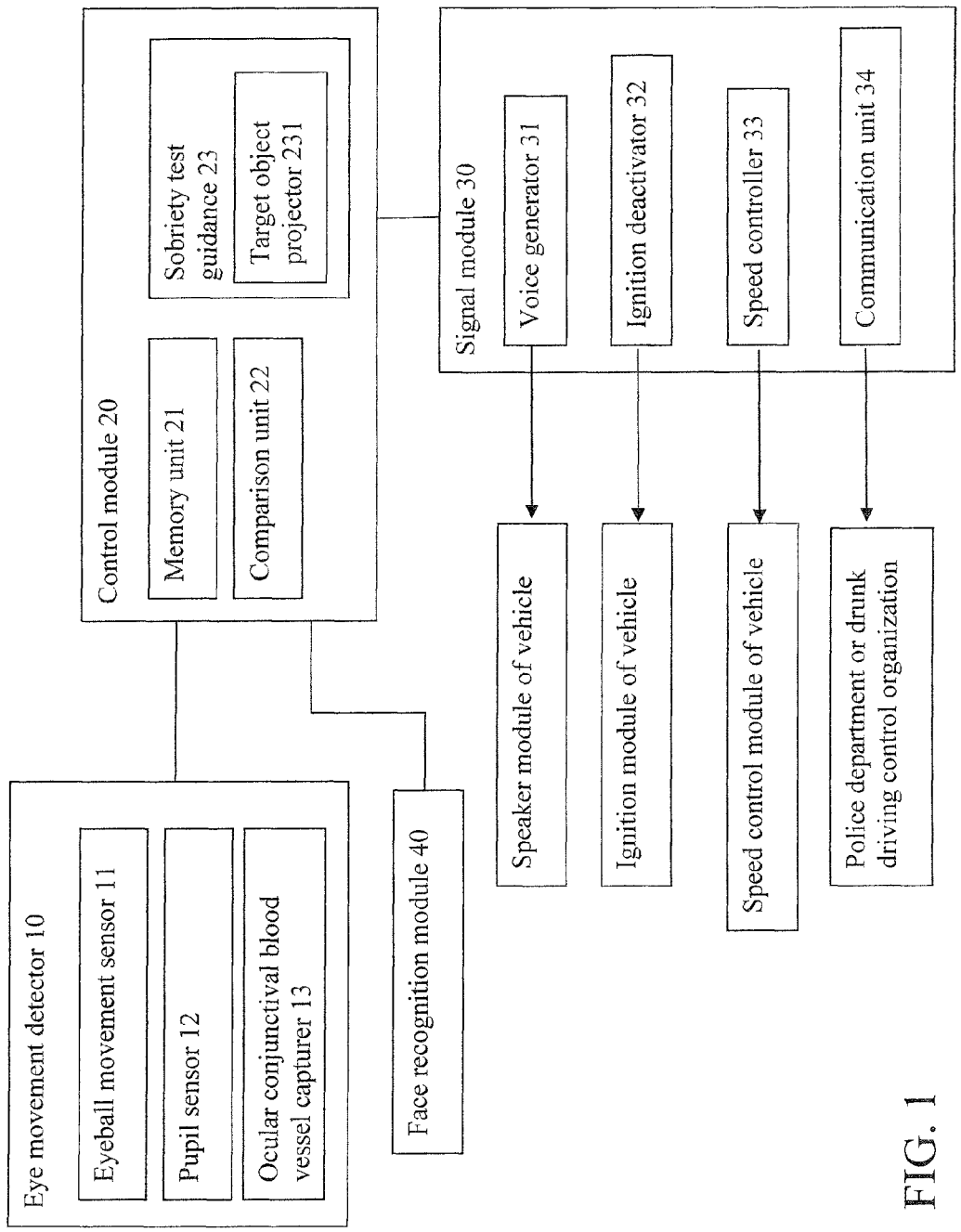
FIG. 1 is a block diagram illustrating a drunk driving prevention system according to a preferred embodiment of the present invention.
Figure 3:
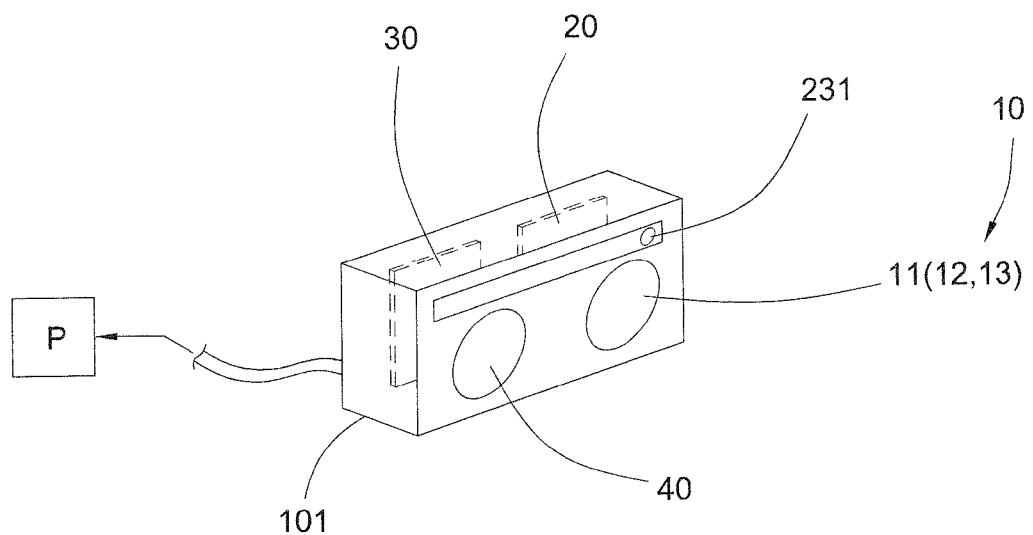
FIG. 3 is a perspective view of the drunk driving prevention system in the vehicle according to the above preferred embodiment of the present invention.

Referring to FIG. 1 of the drawings, a drunk driving prevention system according to a preferred embodiment of the present invention is illustrated, wherein the drunk driving prevention system comprises an eye symptom detector 10, a control module 20, and a signal module 30. The drunk driving prevention system can be installed into a vehicle that the drunk driving prevention system is electrically linked to a power source of the vehicle such that when the vehicle is powered on, the drunk driving prevention system will be automatically turned on. Alternatively, the drunk driving prevention system can be a self-powered device with battery installed and can be linked to the power source of the vehicle to ensure the synchronization between the drunk driving prevention system and the vehicle. Preferably, the drunk driving prevention system comprises a portable casing 101 to be supported at a desired location in the vehicle, wherein the eye symptom detector 10, the control module 20, and the signal module 30 are housed in the portable casing 101, as shown in FIG. 3.

According to the preferred embodiment, the eye symptom detector 10 is arranged for supporting at an interior of the vehicle at a position to detect eye symptoms of a driver. Preferably, the eye symptoms can be eye movements of the driver and/or the eye vessels of the driver.

The eye movement refers to nystagmus which means fast and uncontrollable movements of the eyes including horizontal nystagmus (side to side), vertical nystagmus (up and down), and torsional nystagmus (rotary). In particular, nystagmus is a term for involuntary jerking or bouncing of the eyeball. Accordingly, involuntary eye movements of nystagmus could be caused by excessive alcohol which influents the function of brain to control eye movements.

Figure 2:
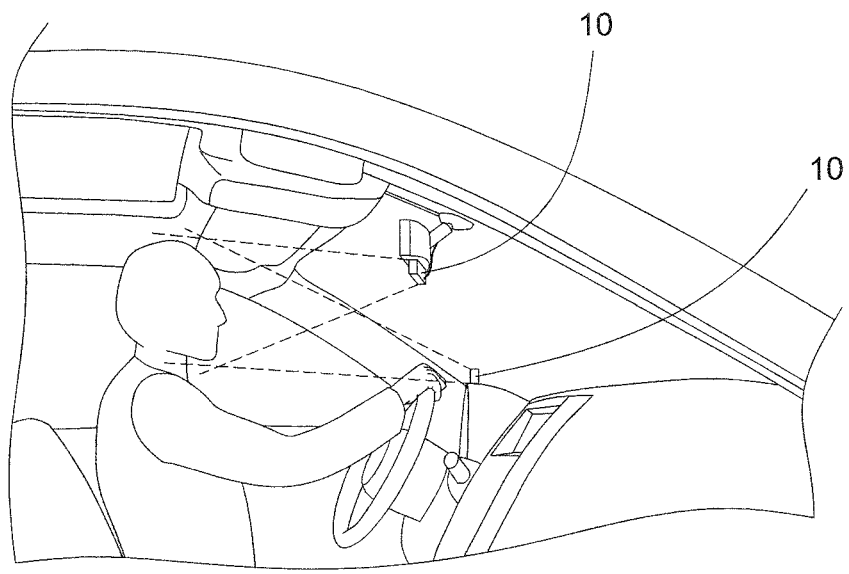
FIG. 2 illustrates an eye symptom detector of the drunk driving prevention system in the vehicle according to the above preferred embodiment of the present invention.

The eye symptom detector 10 can be a video camera, a movement sensor, or an image capturer adapted for detecting the eye movements of the driver. Preferably, the eye symptom detector 10 is installed on a dashboard, rear view mirror, or a sun visor of the vehicle according to an eye level of the driver, as shown in FIG. 2.

In particular, the eye symptom detector 10 comprises an eyeball movement sensor 11 for detecting eyeball movements of the driver, a pupil sensor 12 for detecting sizes of pupils of the driver, and an ocular conjunctival blood vessel capturer 13 for detecting the ocular conjunctival blood vessel, i.e. the diameter size of the ocular conjunctival blood vessel. Under the alcohol influence, the eyeball movements are highly vulnerable and the pupils appear bigger and slower. Also, redness of the eyes is apparent. As a result, the eye movements of a normal person are different from the eye movements of a drunk person. Furthermore, the eye symptom detector 10 can detect or capture the vessel diameter change, wherein the ocular conjunctival blood vessels will dilate under alcohol influence.

The eye symptom detector 10 is activated in response to a start of the vehicle. When the driver sits at the driver side and/or when the vehicle key is detected or inserted into the key ignition hole, the eye symptom detector 10 will be automatically activated and will be automatically searching for the driver at the driver side of the vehicle. When two persons are detected by the eye symptom detector 10, the signal generator 30 will generate a false signal so as to prevent any switching between drivers.

The eye symptom detector 10 is deactivated once the vehicle is turned off. Therefore, the driver will be monitored during driving that the eye symptom detector 10 will keep detecting the alcohol influenced eye symptoms, including the eye movements and ocular conjunctival blood vessels of the driver throughout the driving route. Since human body will take time to absorb and react with alcohol, the alcohol reaction, i.e. the control of eye movements or the dilatation of the ocular conjunctival blood vessel, will gradually appears. In this case, the eye symptom detector 10 will monitor the eye movements and/or the diameter change of the ocular conjunctival blood vessel of the driver in response to the time factor of the alcohol influence.

According to the preferred embodiment, the control module 20 is operatively linked to the eye symptom detector 10 for determining and analyzing whether the eye symptoms of the driver match with the alcohol influenced eye symptoms. In other words, the eye symptom detector 10 will determine and analyze whether the eye movements of the driver are involuntary eye movements that suspect an alcohol concentration of the driver is above a predetermined threshold. Or, the eye symptom detector 10 for will determine and analyze whether the diameter change of the ocular conjunctival blood vessel that suspect an alcohol concentration of the driver is above a predetermined threshold.

Accordingly, the control module 20 contains a plurality of different thresholds to indicate different eye movements and different diameter changes of the ocular conjunctival blood vessels. In particular, the control module 20 comprises a memory unit 21 storing data of normal eye symptoms, i.e. normal eye movements and normal diameter size of the ocular conjunctival blood vessel, and a comparison unit 22 comparing the detected eye symptoms by the eye symptom detector 10 to the normal eye symptoms to determine whether the eye symptoms of the driver are alcohol influenced eye symptoms. In other words, the comparison unit 22 will compare the detected eye movements by the eye symptom detector 10 to the normal eye movements to determine whether the eye movements of the driver are involuntary eye movements. The comparison unit 22 will compare the detected ocular conjunctival blood vessel by the eye symptom detector 10 to the normal ocular conjunctival blood vessel to determine whether the diameter size of the ocular conjunctival blood vessel of the driver is dilated.

The memory unit 21 will store the information of the eye symptoms of driver normally without alcohol influence. Preferably, under normal circumstance (the driver without alcohol influence), the eye symptom detector 10 will detect the normal eye symptoms of the driver during driving and will send the data of the normal eye symptom to the memory unit 21 as a default setting. In other words, the eye symptom reference of the driver is initially set in the memory unit 21. Therefore, the eye symptom reference of the driver will include the normal eye movements and normal ocular conjunctival blood vessel of the driver in the memory unit 21. Therefore, when the eye symptom detector 10 detects the eye movements of the driver, the comparison unit 22 will instantly compare the detected eye symptoms to the eye symptom reference of the driver in order to determine whether the eye symptoms of the driver are alcohol influenced eye symptoms. For example, when the eye symptom detector 10 detects the eye movements of the driver, the comparison unit 22 will instantly compare the detected eye movements to the normal eye movements of the driver in order to determine whether the eye movements of the driver are involuntary eye movements.

Preferably, a data of statistical normal eye symptoms, including statistical eyeball movements, statistical pupil sizes, and statistical ocular conjunctival blood vessel, are preset in the memory unit 21. Therefore, the comparison unit 22 will instantly compare the detected eye movements to the statistical normal eye symptoms in order to determine whether the eye symptoms of the driver are alcohol influenced eye symptoms.

According to the preferred embodiment, the drunk driving prevention system further comprises a facial recognition module 40 linked to the control module 20 for capturing an image of the driver's face when the eye symptom detector 10 detects the eye movements of the driver. The facial recognition module 40 is preferably built-in with the eye symptom detector 10, such that the facial recognition module 40 and the eye symptom detector 10 are operated together to detect the image of the driver's face and the eye movements of the driver at the same time. Accordingly, the image of the driver's face will be saved in the memory unit 21. When the facial recognition module 40 captures the image of the driver's face, the image of the driver's face will be locked to detect the eye symptoms of the driver by the eye symptom detector 10.

It is worth mentioning that when the facial recognition module 40 detects the driver as the owner of the vehicle, i.e. driving the vehicle frequently, the memory unit 21 will be activated to the default setting. For example, the comparison unit 22 will instantly compare the detected eye movements to the normal eye movements of the driver. If the facial recognition module 40 detects a strange/new driver of the vehicle that the default setting does not contain the information of the new driver, the comparison unit 22 will instantly compare the detected eye movements to the statistical normal eye movements.

According to the preferred embodiment, the control module 20 further comprises a sobriety test guidance 23 operatively linked to the eye symptom detector for guiding the driver to perform a sobriety test when the eye symptom detector 10 detects the eye movements of the driver. Accordingly, the sobriety test is developed for the horizontal gaze nystagmus to accurately identify possible drunk drivers.

In order to execute the sobriety test, the sobriety test guidance 23 comprises a target object projector 231 provided at the eye symptom detector 10. Preferably, the target object projector 231 is built-in at the eye symptom detector 10 and is arranged for generating a light spot on the eye symptom detector 10. The target object projector 231 is controllably operated to move the light spot from one side to another while the eye symptom detector 10 will detect the eye movements of the driver. Then, the comparison unit 22 will determine the angle at which the jerking movements begin by comparing with the normal eye movements. Researches proven that jerking movements in the eye before the gaze reaches a 45-degree angle is indicative of a possible blood alcohol content level over 0.05%. Therefore, the jerking movements will be taken account of involuntary eye movements.

Preferably, the signal module 30 comprises a voice generator 31 for generating a voice signal to guide the driver to perform the sobriety test. For example, a voice to remind the driver to focus on the light spot by the target object projector 231 will be generated. The voice generator 31 will also generate a warning signal to notify the driver not to drive the vehicle when alcohol influenced eye symptoms are detected. The voice generator 31 can be wirelessly linked to the speaker module of the vehicle as well.

As shown in FIG. 1, the signal module 30 further comprises an ignition deactivator 32 for operatively linking to an igniter of the vehicle, wherein when the alcohol influenced eye symptoms are determined, the ignition deactivator 31 is activated for preventing an ignition of the vehicle. Therefore, once the alcohol influenced eye symptoms are determined, the driver is unable to start the vehicle. Likewise, if the driver fails the sobriety test, the driver is unable to start the vehicle.

The signal module 30 further comprises a speed controller 33 for operatively linking to the vehicle, wherein when the alcohol influenced eye symptoms are determined, the speed controller 33 is activated for controllably limiting the speed of the vehicle. Even though the driver may force to start the vehicle, the speed of the vehicle will be limited, such as 5 mph, to prevent the over-speeding of the vehicle by the drunk driver.

According to the preferred embodiment, the signal module 30 further comprises a communication unit 34 operatively linked to the control unit 20, wherein the communication unit 34 is arranged for sending a suspected drunk driving signal to a police or a drunk driving control organization when the alcohol influenced eye symptoms are kept detecting for a predetermined control time period, especially during driving. The communication unit 34 can be a mobile communication network or a wireless communication network linked to the closest police department or the drunk driving control organization. As it is mentioned above, the eye symptom detector 10 will be activated to continuously detect the eye symptoms of the driver during driving. For example, when the alcohol influenced eye symptoms are kept detecting for one minute, the suspected drunk driving signal will be automatically sent by the communication unit 34. In other words, even though the driver is able to start the vehicle at the time the driver has not been influenced by alcohol, the eye symptom detector 10 will continuously detect the alcohol influenced eye symptoms of the driver during driving to ensure there is no alcohol influence at all time. In some circumstances, the driver may drink alcohol during driving. Therefore, the drunk driving prevention system will enforce the driver not to drive under alcohol influence during driving.

It is worth mentioning that the signal module 30 can be incorporated with a GPS module to provide location and time information of the vehicle. Therefore, polices or other enforcers can locate the vehicle when they receive the suspected drunk driving signal.

It is appreciated that the drunk driving prevention system can be enforced to be installed into the vehicle that the driver with a restricted license to go to and from work. When a person seats at the driver side of the vehicle, the facial recognition module 40 will detect and recognize the person. If facial recognition module 40 recognizes the person who is the driver with the restricted license, the control unit 20 will execute the sobriety test for the driver and/or the eye symptom detector 10 will be activated to detect the eye symptoms of the driver. Once the alcohol influenced eye symptoms are determined, the driver is unable to start the vehicle. The communication unit 34 will automatically send the suspected drunk driving signal to the police or the drunk driving control organization when the alcohol influenced eye symptoms are detected. In addition, when the drunk driving prevention system is intentionally unplugged from the vehicle or broken, the communication unit 34 will instantly send the suspected drunk driving signal, especially when the driver is enforced with the restricted license.

Figure 4:
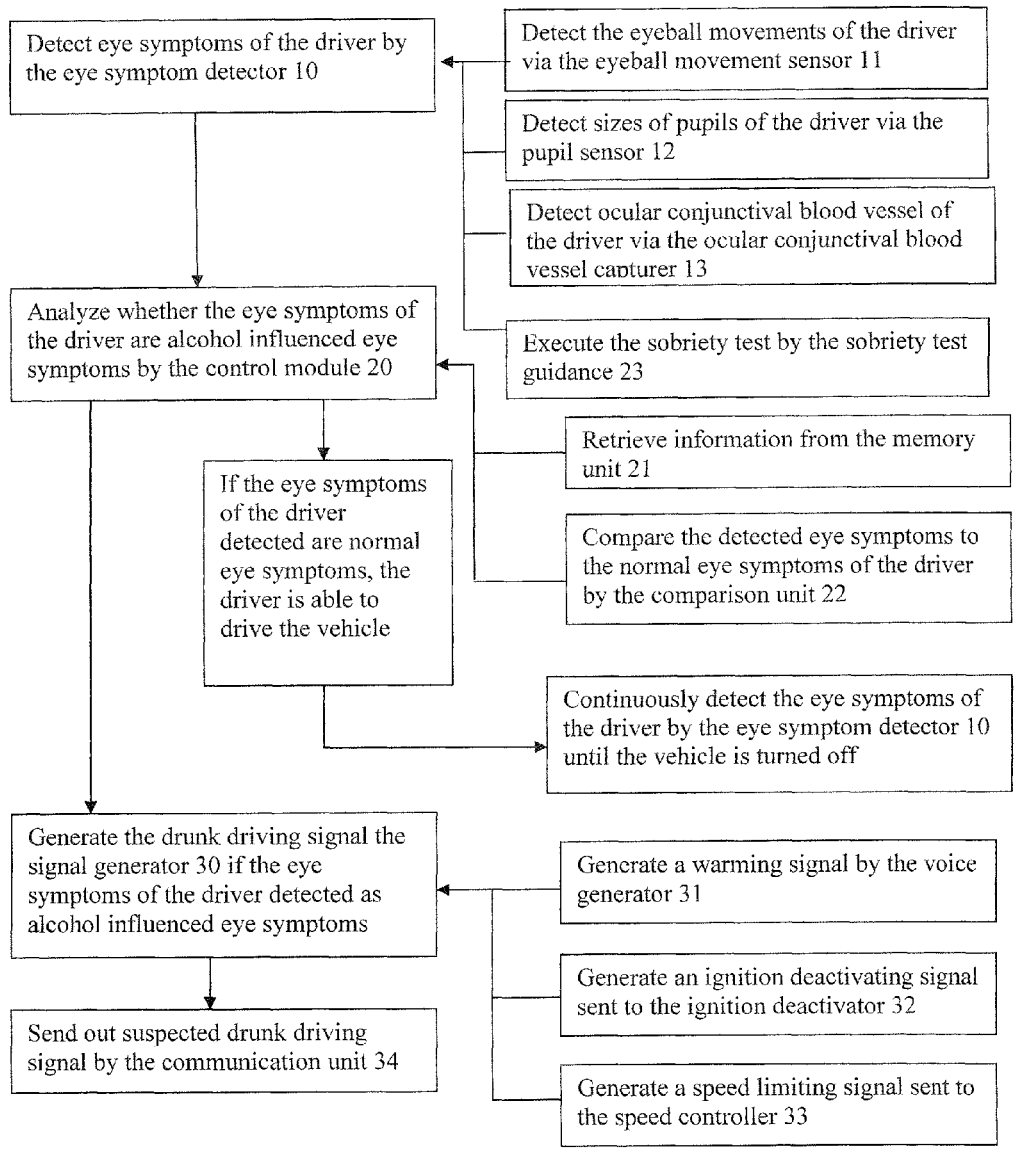
FIG. 4 is a flow diagram illustrating a drunk driving prevention method according to the above preferred embodiment of the present invention

As shown in FIG. 4, the present invention further provides a drunk driving prevention method for preventing drunk driving the vehicle, comprising the following steps.

(1) Detect eye symptoms of the driver by the eye symptom detector 10. Accordingly, when the vehicle is powered on, the eye symptom detector 10 will automatically start to detect the eye symptoms of the driver. Concurrently, the facial recognition module 40 will automatically start to capture the image of the driver's face. In the step (1), the eye symptoms of the driver are detected by the steps of detecting the eyeball movements of the driver via the eyeball movement sensor 11, detecting the sizes of pupils of the driver via the pupil sensor 12, and/or detecting the ocular conjunctival blood vessel.

Preferably, the sobriety test is executed for the driver by the sobriety test guidance 23 of the control module 20 at the same time when the eye symptom detector 10 detects the eye movements of the driver.

(2) Analyze whether the eye symptoms of the driver are alcohol influenced eye symptoms by the control module 20, accordingly, the information is retrieved from the memory unit 21, wherein the comparison unit 22 will instantly compare the detected eye symptoms to the normal eye symptoms of the driver stored in the memory unit 21 in order to determine whether the eye symptoms of the driver are alcohol influenced eye symptoms.

(3) If the eye symptoms of the driver detected are considered as normal eye symptoms, the driver is able to drive the vehicle. The driver is able to start the vehicle and drive. It is worth mentioning that the eye symptom detector 10 will continuously detect the eye symptoms of the driver during driving.

(4) Generate the drunk driving signal by the signal generator 30 if the eye symptoms of the driver detected to be alcohol influenced eye symptoms that suspect an alcohol concentration of the driver is above a predetermined threshold. The drunk driving signal can be an ignition deactivating signal sent to the ignition deactivator 32 for preventing an ignition of the vehicle. The drunk driving signal can be a speed limiting signal sent to the speed controller 33 to limit the speed of the vehicle. The driving signal can also be the suspected drunk driving signal sent by the communication unit 34.

It is worth mentioning that the drunk driving prevention system of the present invention can work in conjunction with breathalyzer to provide a further indication of whether the driver is under the alcohol influence.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A drunk driving prevention system for a vehicle, comprising:

an eye symptom detector adapted for supporting in said vehicle at a position to detect different eye symptoms, including at least one of eyeball movements, ocular conjunctival blood vessel, and pupil sizes, of a driver;

a control module operatively linked to said eye symptom detector for determining and analyzing whether said eye symptoms of said driver match with alcohol influenced eye symptoms, wherein said control module comprises a test guidance operatively linked to said eye symptom detector for guiding said driver to perform a test when said eye symptom detector detects eye movements of said driver, wherein said test guidance comprises a target object projector provided at said eye symptom detector for generating a light spot thereon and for controlling a movement of said light spot, wherein said eye symptom detector is arranged for detecting the eyeball movements of the driver following the movement of said light spot; and a signal module operatively linked to said control module for generating a drunk driving signal in response to said eye symptoms of said driver that suspects an alcohol concentration of said driver is above a predetermined threshold.

2. The drunk driving prevention system, as recited in claim 1, wherein said control module comprises a memory unit storing data of normal eye symptoms, and a comparison unit comparing detected eye symptoms by said eye symptom detector to said normal eye symptoms to determine whether said eye symptoms of said driver are alcohol influenced eye symptoms.

3. The drunk driving prevention system, as recited in claim 1, wherein said eye symptom detector is activated in response to a start of said vehicle and is deactivated in response to said vehicle being turned off.

4. The drunk driving prevention system, as recited in claim 2, wherein said eye symptom detector is activated in response to a start of said vehicle and is deactivated in response to said vehicle being turned off.

5. The drunk driving prevention system, as recited in claim 1, wherein said test guidance is a sobriety test guidance, wherein said test guidance further comprises a voice generator operatively linked to said target object projector for generating a voice signal to guide the driver to focus and follow the movement of said light spot.

6. The drunk driving prevention system, as recited in claim 3, wherein said test guidance is a sobriety test guidance, wherein said test guidance further comprises a voice generator operatively linked to said target object projector for generating a voice signal to guide the driver to focus and follow the movement of said light spot.

7. The drunk driving prevention system, as recited in claim 4, wherein said test guidance is a sobriety test guidance, wherein said test guidance further comprises a voice generator operatively linked to said target object projector for generating a voice signal to guide the driver to focus and follow the movement of said light spot.

8. The drunk driving prevention system, as recited in claim 1, wherein said eye symptom detector is selected from a group consisting of an eyeball movement sensor for detecting eyeball movements of said driver, an pupil sensor for detecting sizes of pupils of said driver, and an ocular conjunctival blood vessel capturer for detecting an ocular conjunctival blood vessel of said driver.

9. The drunk driving prevention system, as recited in claim 7, wherein said eye symptom detector is selected from a group consisting of an eyeball movement sensor for detecting eyeball movements of said driver, an pupil sensor for detecting sizes of pupils of said driver, and an ocular conjunctival blood vessel capturer for detecting an ocular conjunctival blood vessel of said driver.

10. The drunk driving prevention system, as recited in claim 1, wherein said signal module comprises an ignition deactivator for operatively linking to an igniter of said vehicle, wherein when said alcohol influenced eye symptoms are determined, said ignition deactivator is activated for preventing an ignition of said vehicle.

11. The drunk driving prevention system, as recited in claim 9, wherein said signal module comprises an ignition deactivator for operatively linking to an igniter of said vehicle, wherein when said alcohol influenced eye symptoms are determined, said ignition deactivator is activated for preventing an ignition of said vehicle.

12. The drunk driving prevention system, as recited in claim 1, further comprises a facial recognition module linked to said control module for capturing an image of the driver's face when said eye symptom detector detects said eye symptoms of said driver.

13. The drunk driving prevention system, as recited in claim 11, further comprises a facial recognition module linked to said control module for capturing an image of the driver's face when said eye symptom detector detects said eye symptoms of said driver.

14. The drunk driving prevention system, as recited in claim 1, wherein said signal module further comprises a communication unit for sending a suspected drunk driving signal to a police or a drunk driving control organization when said alcohol influenced eye symptoms are kept detecting for a predetermined control time period.

15. The drunk driving prevention system, as recited in claim 13, wherein said signal module further comprises a communication unit for sending a suspected drunk driving signal to a police or a drunk driving control organization when said alcohol influenced eye symptoms are kept detecting for a predetermined control time period.

16. A drunk driving prevention method for preventing drunk driving a vehicle, comprising the steps of:
  (a) detecting different eye symptoms, including at least one of eyeball movements, ocular conjunctival blood vessel, and pupil sizes of a driver by an eye symptom detector;
  (b) analyzing whether said eye symptoms of said driver are alcohol influenced eye symptoms by a control module;
  (c) if said eye symptoms of said driver detected are normal eye symptoms, said driver able to drive said vehicle;
  (d) generating a drunk driving signal by a signal generator if said eye symptoms of said driver are detected as alcohol influenced eye symptoms that suspects an alcohol concentration of said driver is above a predetermined threshold; and
  (e) if said eye symptoms of said driver are detected as alcohol influenced eye symptoms, generating a light spot on said eye symptom detector and controlling a movement of said light spot in order to detect the eyeball movements of the driver following the movement of said light spot by said eye symptom detector, so as to identify possible drunk driver.

17. The method, as recited in claim 16, wherein said eye symptom detector is activated in response to a start of said vehicle and is deactivated in response to said vehicle being turned off.

18. The method, as recited in claim 16, wherein the step (a) further comprises a step of generating a voice signal by a voice generator to guide the driver to focus and follow the movement of said light spot.

19. The method, as recited in claim 17, wherein the step (a) further comprises a step of generating a voice signal by a voice generator to guide the driver to focus and follow the movement of said light spot.

20. The method, as recited in claim 16, wherein the step (a) further comprises at least one of the steps of detecting eyeball movements of said driver, detecting sizes of pupils of said driver, and detecting the ocular conjunctival blood vessel of said driver.

21. The method, as recited in claim 19, wherein the step (a) further comprises at least one of the steps of detecting eyeball movements of said driver, detecting sizes of pupils of said driver, and detecting the ocular conjunctival blood vessel of said driver.

22. The method, as recited in claim 16, wherein the step (c) further comprises a step of deactivating an igniter of said vehicle when said alcohol influenced eye symptoms are determined for preventing an ignition of said vehicle.

23. The method, as recited in claim 21, wherein the step (c) further comprises a step of deactivating an igniter of said vehicle when said alcohol influenced eye symptoms are determined for preventing an ignition of said vehicle.

24. The method, as recited in claim 16, further comprising a step of capturing an image of the driver's face by a facial recognition module when said eye symptom detector detects said eye symptoms of said driver.

25. The method, as recited in claim 23, further comprising a step of capturing an image of the driver's face by a facial recognition module when said eye symptom detector detects said eye symptoms of said driver.

26. The method, as recited in claim 16, further comprising a step of sending a suspected drunk driving signal to a police or a drunk driving control organization when said alcohol influenced eye symptoms are kept detecting for a predetermined control time period.

27. The method, as recited in claim 25, further comprising a step of sending a suspected drunk driving signal to a police or a drunk driving control organization when said alcohol influenced eye symptoms are kept detecting for a predetermined control time period.

* * * * *